United States Patent [19]

Ho

[11] Patent Number: 4,645,829
[45] Date of Patent: Feb. 24, 1987

[54] METHOD FOR SEPARATING POLYPEPTIDES

[75] Inventor: Sa Van Ho, Maryland Heights, Mo.

[73] Assignee: Monsanto Company, St. Louis, Mo.

[21] Appl. No.: 665,689

[22] Filed: Oct. 29, 1984

[51] Int. Cl.$^4$ .......................... A23J 1/09; B01D 21/01
[52] U.S. Cl. ..................................... 530/344; 530/412; 210/672; 210/723; 210/730; 210/732; 210/733; 210/735; 210/905; 210/927
[58] Field of Search ....................... 260/112 R, 112 B; 210/633, 672, 723, 730, 732, 733, 734, 735, 905, 927; 525/54.11; 530/344, 412

[56]  References Cited

U.S. PATENT DOCUMENTS

| | | | |
|---|---|---|---|
| 3,655,509 | 4/1972 | Fields et al. | 210/734 |
| 3,994,806 | 11/1976 | Rausch et al. | 210/734 |
| 4,357,272 | 11/1982 | Polson | 260/112 R |
| 4,518,769 | 5/1985 | Wu et al. | 525/326.1 |

Primary Examiner—John Kight
Assistant Examiner—Nathan M. Nutter
Attorney, Agent, or Firm—Dennis R. Hoerner, Jr.; James W. Williams, Jr.

[57]  ABSTRACT

A method of separating a first polypeptide fraction from a second polypeptide fraction of a mixed solution is disclosed. A predetermined charged polymer is admixed with the mixed solution preferably in the presence of a neutral polymer. The charged polymer interacts with the first fraction to form a precipitate. The neutral polymer enhances the effectiveness of the charged polymer in precipitating the first fraction. By proper selection of the polymer combination the desired polypeptide fraction can be precipitated from solution leaving the other polypeptide fraction in solution or vice versa.

25 Claims, 1 Drawing Figure

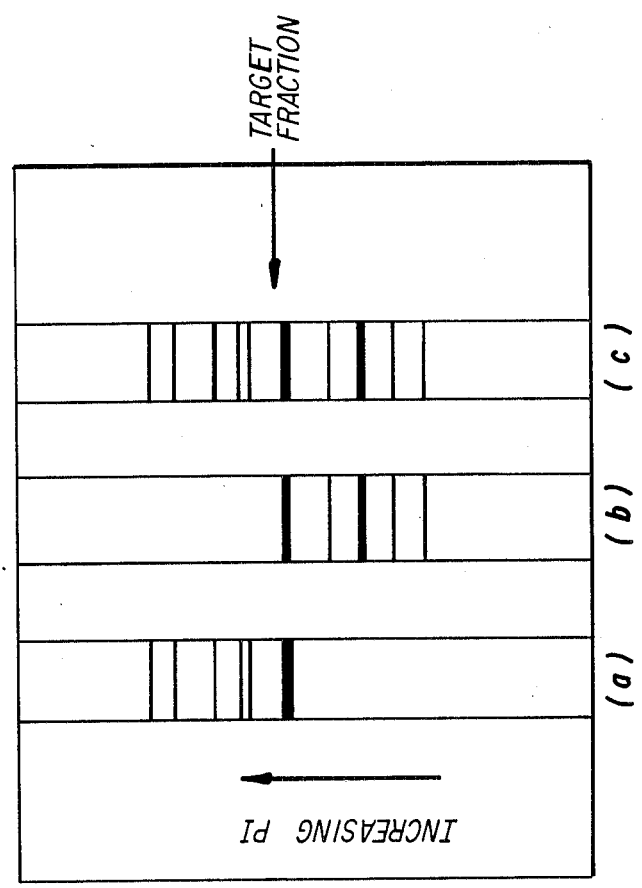

METHOD FOR SEPARATING POLYPEPTIDES

BACKGROUND OF THE INVENTION

The present invention relates to a method for separating polypeptides (e.g. proteins), and more particularly to a method for separating a first polypeptide fraction from a second polypeptide fraction of a mixed solution containing the fractions by selective precipitation of one of the fractions.

Single-phase methods disclosed heretofore for purifying proteins using polymeric precipitants fall into two general methods which are both based on differential solubility of proteins. In one method, a neutral polymer is added to the protein solution to cause a decrease in the solubility of the target protein which therefore precipitates out of solution. By "target protein" is meant the protein or protein fraction that is precipitated from solution as a result of its interaction with a polymeric precipitant. Neutral polymeric precipitation methods have severe disadvantages. Precipitation using neutral polymers is not usually very selective. Use of neutral polymeric precipitants often requires that the solution pH be near the isoelectric point of the target protein to obtain significant precipitation. In addition, this method is not applicable to dilute protein solutions since relatively high concentrations of both protein and neutral polymer are normally required for precipitation to occur.

In the other method, a charged polymer is used to form a complex with the target protein. The complex, which is usually much less soluble than the uncomplexed target protein, precipitates out of solution. While charged polymeric precipitants are more specific with respect to the target protein and require only stoichiometric amounts of polymer, precipitation often occurs only in a very narrow range of operating conditions, i.e. pH, protein concentration and polymer concentration. In addition, precipitation is reduced in the presence of chaotropic agents such as urea.

Methods have also been disclosed for protein purification using aqueous two-phase systems. These methods are based on the incompatibility of polymers in aqueous solution and the partition coefficient of the target protein versus other contaminating proteins. The reason for the incompatibility is believed to be the inability of the polymer coils to penetrate each other. As a result, if one mixes polymer A with an incompatible polymer B at sufficiently high polymer concentration an aqueous two-phase system can be formed. Likewise, aqueous multiple-phase systems can be obtained by mixing several incompatible polymers at sufficiently high concentration. The polymers for these aqueous multiple-phase systems are chosen such that the solubility of the target protein is much higher in one polymer phase than the others. The partition coefficient can be somewhat enhanced by the addition of small amounts of salts or polyelectrolytes. Unfortunately, multi-phase methods require separation of the protein-rich phase and subsequent recovery of the protein therefrom.

It has now been found that the effectiveness of polypeptide separation using charged polymeric precipitant can be enhanced by using, in addition to the charged polymer, at least one soluble neutral polymer. The effectiveness of the charged polymer may be enhanced by improving or otherwise modifying the precipitation of the target fraction and/or the selectivity of the charged polymeric precipitant for the target polypeptide fraction.

It is, therefore, the overall object of the present invention to provide an improved method for separating polypeptides.

Accordingly, it is an object of the present invention to provide a separation method capable of high yields.

It is another object of the present invention to provide a separation method capable of high selectivity.

It is yet another object of the present invention to provide a method capable of operating at a low target polypeptide concentration.

It is still another object of the present invention to provide a separation method capable of operating at a relatively low charged polymer concentration.

It is yet another objective of the present invention to provide a separation method capable of operating under a wide range of conditions in terms of pH and materials present such as chaotropic agents, etc.

These and other objects and advantages of the present invention will be evident to those skilled in the art from the following description and examples.

BRIEF DESCRIPTION OF THE DRAWING

The sole FIGURE is a simple illustration of exemplary isoelectric focusing distributions.

The demarcations of (a), (b), and (c) represent target pI fractions. In (a), the target fraction has a pI below that of the contaminating fraction. In (b), the target fraction has a pI above that of the contaminating fraction. In (c), the target fraction has a pI that is above the pI of one contamination fraction but below the pI of another contaminating fraction.

DESCRIPTION OF THE INVENTION

The present invention provides a method for separating a first polypeptide fraction from a second polypeptide fraction of a mixed solution by selective precipitation of one of the fractions. In the present method, at least one soluble charged polymer is used to precipitate one of the polypeptide fractions while at least one soluble neutral polymer is used to enhance the effectiveness of the charged polymer precipitant. As used in this context, the term "soluble polymer" means a polymer which is soluble in the solution of those polypeptide fractions.

The present method is capable of precipitating a particular polypeptide fraction while leaving the other fraction in solution by proper selection of charged and neutral polymers. Polymers which may be utilized in the practice of the present method include all polymers capable of effecting the desired precipitation such as homo-polymers, copolymers or block polymers. While the molecular weight of the chosen polymer is a consideration as described hereinafter, it will be evident from the following description that the primary consideration should be the inherent chemical properties of the polymer.

While it will be evident from the following description that the present invention has very broad application, selective interaction with chosen polymers becomes more difficult as the ionic property difference between the polypeptide fractions decreases. Although the method is described with respect to polypeptides in general, it is foreseeable that one could construct or find situations where application of this method could be impractical. For example, separation of allelic forms of a particular polypeptide would be impractical, in some cases, if the differences in primary configuration are not enough to result in sufficient differences in chemical properties between the polypeptide fractions. In those cases where polypeptide fractions are extremely close in chemical characteristics, one may be able to selectively derivatize one of the fractions to impart sufficient ionic differences between the two fractions to permit the application of this method.

Although the present invention is more easily applied to mixed solutions between the two fractions comprising higher molecular weight polypeptides such as proteins, it should be clearly understood that this method is not so limited. Rather, this invention is applicable to mixed solutions which comprise dipeptides, tripeptides, tetrapeptides and higher polypeptides so long as a sufficient ionic property difference exists. Biologically active polypeptides of interest include, but are not limited to, hormones and regulatory factors such as interferon, growth hormone releasing factors, prolactins, placental lactogens, insulin (or either of its individual polypeptide chains) and somatomedins, as well as analogs of the naturally occurring molecules in which one or more amino acids have been replaced. Somatotropins such as human, bovine, porcine, ovine and avian (e.g. chicken) somatotropins are of particular interest.

By "mixed solution" is meant a solution comprising a target polypeptide fraction and a contaminating polypeptide fraction. Each fraction includes at least one polypeptide. Mixed solutions include, but are not limited to solutions comprising cell extracts and fermentation broth. Suitable cell extracts include those obtained by disruption of bacterial, yeast, plant and animal cells. Cells may be naturally occurring or genetically transformed to produce a non-native polypeptide. If cell extract is used in the practice of this invention, it is preferred that such extract be pretreated by conventional methods to remove nucleic acids and/or insoluble contaminating cellular material in order to minimize competitive interaction with the charged polymer.

For purpose of clarity and conciseness, the following explanation and examples of the present invention refer to single-stage operations. However, it should be understood that the present method may be operated in multistage fashion where the required separation is unattainable in a single stage. It should be further understood that an advantage of the invention is that one may employ different polymer combinations in the various stages of a multi-stage embodiment since the composition of the proteinaceous solution would necessarily change from stage to stage. Multi-stage operation is particularly useful when the target fraction comprises a plurality of polypeptides. In such an operation, one might precipitate one component of the target fraction in each stage.

The charged polymer is chosen such that at the predetermined operating pH its charge is opposite in polarity to that of the target polypeptide fraction, thereby interacting with the target fraction to form a precipitate. In choosing the charged polymer, one should first determine the charge distribution of the polypeptides comprising the mixed solution. Polypeptides are usually charged molecules due to presence of ionizable substituent groups contained on the individual amino acids. However, at some pH the polypeptide will have a net charge of zero and will behave as zwitterions. The pH at which the polypeptide has no net charge is termed the isoelectric point (pI). The pI for a polypeptide will depend on the individual pKs of the amino acids comprising the polypeptide. At a pH above its pI, a polypeptide will have a net negative charge. At a pH below its pI, a polypeptide will have a net positive charge. The extent of charge for a given deviation from the pI will depend on the particular polypeptide.

The relative pIs of the polypeptides comprising the solution can be determined by isoelectric focusing. The approximate amount of polypeptide having a particular pI can be spectrophotometrically determined by using a differential scanning densitometer. Referring to FIG. 1, there are provided exemplary results from an isoelectric focusing procedure.

In FIG. 1 (a) of the drawing, the target fraction has a pI below that of the contaminating fraction. In such a case, one could conduct the separation method at a pH below the pI of contaminating fraction but above the pI of the target fraction. The contaminating fraction would have a net negative charge, and the target fraction would have a net positive charge. To precipitate the target fraction one would select a polymer having a negative charge at the operating pH for the separation.

In FIG. 1 (b) of the drawing, the target fraction has a pI above that of the contaminating fraction. In such a case, one could conduct the separation at a pH below the pI of the target fraction but above the pI of the contaminating fraction. The contaminating fraction would have a net positive charge while the target fraction would have a net negative charge. To precipitate the target fraction one would select a polymer having a positive charge at the operating pH for the separation.

In FIG. 1(c) of the drawing, the target fraction has a pI that is above the pI of one contaminating fraction but below the pI of another contaminating fraction. In such a situation, it is preferred that the separation be carried out in more than one stage. One could conduct the first separation at a pH below the pI of the target fraction but above the pI of one of the contaminating fractions. Using a polymer having a positive charge at the predetermined pH and a suitable neutral polymer selected as described hereinafter one could precipitate from solution the one contaminating fraction leaving the target fraction and other contaminating fraction in solution. The second stage separation would be conducted at a pH above the pI of the target fraction but below the pI of the other contaminating fraction. A polymer having a negative charge at the operating pH is selected to precipitate the target fraction from solution in conjunction with a neutral polymer selected as described hereinafter. It should be understood, however, that the supernatant from a previous stage may have to be cleansed of polymeric material if they would interfere with the separation in the following stages.

In some situations, all polypeptides will have the same polarity within the operable pH range. In such a case, one would select a pH to maximize the difference in charge between the target fraction and the contaminating fraction. Since one of the fractions should have a greater net charge at a predetermined pH, a charged polymer of opposite polarity at that pH will interact more strongly with that fraction. In addition, a stoichiometric amount of charged polymer is used such that only enough charged polymer is present to interact with the target polypeptide fraction.

While the primary parameter for the charged polymer is its polarity at the operating pH, other parameters which should be considered in the selection of the charged polymer precipitant include, but are not limited to, the type of charged group on the polymer, density of charge as indicated by the number of charged groups per polymer molecule, the molecular weight of the polymer and the pH of the solution. The type of charged group is important since the pK for the various groups will determine the net charge for the polymer at a particular operating pH. The number of charged groups on the polymer precipitant is important since the precipitating capacity will, in many cases, increase with higher net charge. Charged polymer molecular weight is important since, a higher molecular weight polymer will often be capable of causing precipitation at lower polypeptide concentrations than will lower molecular weight charged polymers when all other properties are equal. While only one charged polymer will usually be used, one may choose to employ more than one charged polymer. The parameters used in the selection of a suitable charged polymer precipitant for practice of this invention are, to a certain extent, much the same as those used when the charged polymer is used alone. However, a further consideration is the interaction between the charged polymer and the neutral polymer as described hereinafter.

The relative charge of the target polypeptide fraction compared to other contaminating polypeptides may be increased or decreased by adjusting the pH of the solution to a level either closer or farther away from the pI of the target polypeptide fraction. Likewise, the polarity of the target polypeptide fraction can be changed by adjusting the pH of the solution to either above or below the pI of the polypeptide fraction. It should be evident that a substantially stoichiometric amount of charged polymer may be used in the practice of this invention. However, the particular optimal concentration will necessarily depend on the polymer system and operating conditions employed. Charged polymers that may be used include, but are not limited to, polyacrylic acid, dextran sulfate, carboxymethyl cellullose, polymethacrylic acid, diethylaminoethyldextran and polyethyleneimine. Alternately, charged polymers which possess the requisite properties described above can be easily synthesized for a particular application.

The present invention embraces the surprising discovery that the effectiveness of polypeptide separation using charged polymeric precipitants can be greatly enhanced by using, in addition to a charged polymer, at least one soluble neutral polymer. The effectiveness of the charged polymer may be enhanced by improving or otherwise modifying the precipitation of the target fraction and/or the selectivity of the charged polymeric precipitant for precipitating the target polypeptide fraction. It is believed that neutral polymer enhances the effectiveness of the charged polymer precipitant due to the differences in nonionic character between (1) the neutral polymer and the interaction product of the charged polymer and target polypeptide fraction, and/or (2) the neutral polymer and the polypeptide fraction to remain in solution. The preferred nonionic property difference to be exploited in the practice of this invention is the hydrophobicity/hydrophilicity difference. The relative hydrophobicity/hydrophilicity characteristics of the subject fractions, as well as the potential neutral and changed polymers, may be determined by reverse-phase chromatography. This technique is well documented in the literature and described in the following articles: Regnier et al, *Anal. Biochemistry* 103, 1–25 (1980), Regnier, *Science* 222, No. 4621, 245–252 (1983), and Fausnaugh et al., *Anal. Biochemistry* 137, 464–472 (1984). In choosing the neutral polymer to be used in the practice of this invention, it is preferred but not critical, that its hydrophobicity/hydrophilicity characteristic be substantially opposed to that of the interaction product of the charged polymer and target fraction. The nonionic character of the interaction product would depend on the nonionic properties of the charged polymer and target fraction which comprises the product, as well as their specific conformational interaction. The nonionic character of this interaction product may be approximated, in some cases, by the nonionic character of the charged polymer backbone. The accuracy of this approximation will be more correct for systems having the concentration of charged polymer optimized. By "charged polymer backbone" is meant the polymer prior to derivatization with the charged substituents. For example, dextran would be the backbone polymer for the charged polymer diethylaminoethyldextran. If the charged polymer backbone is essentially hydrophilic, a neutral polymer of hydrophobic character is preferred. While not fully understood, the hydrophobicity/hydrophilicity difference between the neutral polymer and the interaction product often results in an enhanced effectiveness of the charged polymeric precipitant by further increasing the degree of precipitation of the target polypeptide fraction.

In some cases, the presence of the neutral polymer may result in precipitation of the target polypeptide fraction where the charged polymer alone failed to form a precipitate. In other cases, the presence of the neutral polymer may allow the separation to be conducted at a lower charged polymer precipitant concentration. For this purpose, the concentration of the neutral polymer and its molecular structure are the two most important parameters to be considered. Higher neutral polymer concentration will often cause or enhance precipitation in a solution having a low concentration of the target fraction. The response to higher neutral polymer concentration may be less dramatic for solution having relatively high concentrations of the target fractions. A neutral polymer of linear structure is, in general, a more effective precipitant than one of branched structure with the same molecular weight. All other properties being equal a neutral polymer of higher molecular weight will be a more effective secondary precipitant.

It is further preferred that the neutral polymer have similar nonionic characteristics to that of the polypeptide fraction to remain in solution. While not fully understood, this relationship seems to often result in an enhanced selectivity of the charged polymer precipitant for the target fraction.

It should be evident to those skilled in the art that while water-soluble neutral polymers are, in general, hydrophilic in nature, these polymers can be ranked on a hydrophobicity scale by such techniques as reverse-phase chromatography and by solubility measurements, see Zaslavsky et al. *J. Chromatography*, 285, pp 63–68 (1984). For example, commonly used water-soluble neutral polymers include: (in order of increasing hydrophobicity) dextran sulfate, carboxymethyl dextran, dextran, hydroxypropyldextran, methylcellullose, polyvinylalcohol, polyethylene glycol and polypropylene glycol. If no commercially available neutral polymer is found to be suitable, one could synthesize a neutral polymer possessing the requisite nonionic properties. While only one neutral polymer will often be used, one may choose to employ more than one neutral polymer.

In the practice of this invention, it is preferred that the mixed solution be contacted with the predetermined charged polymer precipitant in the presence of the predetermined neutral polymer. This may be accomplished by adding the mixed solution to a prepared mixture of the predetermined polymers, or by adding the neutral polymer to the solution followed by addition of the charged polymer precipitant. While the addition procedure should not be construed as critical to the practice of this invention, the importance of such procedure will depend on the reactiveness of the system and the rate of precipitate formation.

This method of invention can be carried out according to the directives above to precipitate from solution the contaminating proteins or to precipitate from solution the desired polypeptide fraction. It will be evident to those skilled in the art that depending upon the condition of the polypeptide solution that one option may be more convenient than the other. It should be fully understood that while the present invention has been described with respect to the aqueous systems of the following exemplary embodiments, it is not so limited. The present invention can be conducted in non-aqueous solvents following the directives above. Indeed, use of organic solvent may permit one to enlarge the property differences needed for practice of this invention.

The following examples are included to better elucidate the practice of the present invention. It should be understood that these examples are included for illustrative purposes only and are not, in any way, intended to limit the scope of the present invention.

EXAMPLE 1

The present invention has been successfully demonstrated by the separation of N-methionyl bovine somatotropin (MBS), prepared as described by Seeburg et al. in 2(1) DNA 37–45 (1983), from contaminating *E. coli* proteins. At a pH between about 9 and 12, MBS is less negatively charged and more hydrophobic than the contaminating *E. coli* proteins. The contaminating proteins can be precipitated out of solution with a positively charged polymeric precipitant since it will interact more strongly with these proteins than with MBS. A relatively hydrophobic neutral polymer will enhance the effectiveness of the charged polymeric precipitant.

An aqueous proteinaceous solution containing 2.3 mg/ml of MBS and 4.3 mg/ml of contaminating *E. coli* proteins was used. The solution had a pH of 10.5 (4.5 M urea, 50 mM Tris(hydroxymethylaminomethane)) and was maintained at a temperature between 0°–4° C. Polyethylene glycol (PEG, molecular weight 3500–4000), a neutral polymer of relatively hydrophobic character, was added such that its concentration was 10 wt % based on the resulting mixture containing both neutral and charged polymers. Approximately 0.2 mg of Diethylaminoethyldextran (DEAE-Dextran approx. ave. molecular weight 500,000 having one DEAE substitution for every three glucose units) was added per mg of contaminating proteins. The precipitated contaminant proteins were removed by low-speed centrifugation. Analysis of the supernatant by both spectrophotometry and high performance liquid chomatography indicated an MBS yield of 95 wt % with a purity of 95 wt %. The yield and purity of MBS obtained by the process of the present invention was significantly improved over the use of either polymer alone (see Comparative Examples A, B and C).

EXAMPLE 2

The procedure outlined in Example 1 was followed except that the polyethylene glycol concentration was about 6.6 wt %. Analysis of the clear supernatant indicated an MBS yield of 94 wt % with an 87 wt % purity.

EXAMPLE 3

The procedure outlined in Example 1 was followed except that polyethylene glycol was added such that its final concentration in the solution was 1.0 wt % based on the total weight of the final mixture. Analysis of the clear supernatant indicated an MBS yield of 96 wt % with a 78 wt % purity.

EXAMPLE 4

The procedure outlined in Example 2 was followed except that the concentration of DEAE-Dextran was 0.35 mg/mg of contaminating proteins and PEG (ave. molecular wt ~1500) was used. Analysis of the clear supernatant indicated an MBS yield of 78 wt % with a 93 wt % purity.

EXAMPLE 5

The procedure outlined in Example 1 was followed except that the solution pH was adjusted to 12.2 using aqueous sodium hydroxide and 1.0 gram of DEAE-Dextran per gram of contaminating proteins was used. Analysis of the supernatant indicated an MBS yield of 98 wt % with a 98 wt % purity.

EXAMPLE 6

The procedure outlined in Example 1 was followed except that the experiment was conducted at room temperature (25° C.) Analysis of the supernatant indicated an MBS yield and purity essentially the same as those given for Example 1.

EXAMPLE 7

The procedure outlined in Example 1 was followed except that polypropylene glycol (PPG, molecular weight 425) was used in place of polyethylene glycol. Analysis of the supernatant indicated an MBS yield of 87 wt % with a 93 wt % purity.

EXAMPLE 8

The procedure outlined in Example 2 was followed except that polyvinyl alcohol (PVA molecular weight 5,000) and 0.32 gm of DEAE-Dextran per gram of contaminating proteins were used. Analysis of the supernatant indicated an MBS yield of 75 wt % with a 90 wt % purity.

EXAMPLE 9

The procedure outlined in Example 1 was followed except that polyethyleneimine (PEI, molecular weight 40,000–60,000) was used in place of DEAE-Dextran. The concentration of PEI used was 0.225 gm per gram of contaminating proteins. Analysis of the supernatant indicated an MBS yield of 63 wt % with a 99 wt % purity.

EXAMPLE 10

The procedure outlined in Example 1 was followed except that a cationic polyamine resin (sold under the trademark SANTOFLOC ® by Monsanto Company) was used in place of DEAE-Dextran. The concentration of polyamine used was 0.1 gm per gm of contaminating proteins. Analysis of the supernatant indicated an MBS yeild of 65 wt % with a 99 wt % purity.

EXAMPLE 11

The procedure outlined in Example 2 was followed except that 0.5 gm of DEAE-Dextran per gram of contaminating proteins was used. Analysis of the ear supernatant indicated an MBS yield of 54 wt % with a 96 wt % purity.

COMPARATIVE EXAMPLE A

The procedure outlined in Example 1 was followed except that no neutral polymer was used. The solution turned cloudy upon addition of DEAE-Dextran. Analysis of the supernatant indicated an MBS yield of 96 wt % with 69 wt % purity.

COMPARATIVE EXAMPLE B

The procedure outlined in Comparative Example A was followed except that 0.5 mg of DEAE-Dextran per mg of contaminating protein was used. Analysis of the supernatant indicated an MBS yield of 88 wt % with a 66 wt % purity.

COMPARATIVE EXAMPLE C

The procedure outlined in Example 1 was followed except that only PEG was used (no charged polymer). No precipitation was observed.

COMPARATIVE EXAMPLE D

The procedure outlined in Comparative Example C was followed except that the PEG concentration was varied up to about 50 wt %. Again, no precipitation was observed in the absence of charged polymer.

EXAMPLE 12

An aqueous protein mixture was prepared containing phycocyanin (MW~103,000; pI~5.2-5.3) and hemoglobin (MW~64,500; pI~6.8-7.0) in sodium phosphate buffer (25 mM). The mixture had a pH of 7.5 and a total protein concentration of 6 mg/ml about 20 wt % of which was phycocyanin. While at this pH both proteins are negatively charged, phycocyanin is most negatively charged since phycocyanin has a substantially lower pI than hemoglobin. Analysis of the protein composition by reverse-phase chromatography showed phycocyanin to be much more hydrophobic than hemoglobin. Hence, a positively charged polymer such as DEAE-Dextran can be used along with a neutral polymer to selectively precipitate the phycocyanin protein. DEAE-Dextran was added to the protein mixture in the presence of PEG (ave. MW~8,000; 5 wt % conc.) such that the final mixture contained 0.4 grams of DEAE-Dextran (ave. MW~500,000; ~1 DEAE unit/3 glucose units) per gram of phycocyanin. Determination of the precipitate composition by analysis of the supernatant indicated a phycocyanin yield of 45 wt % with a 88 wt % purity in the precipitate. Attention is directed to Comparative Examples E and F wherein no precipitation occurred upon the addition of either polymer alone.

EXAMPLE 13

The procedure outlined in Example 12 was followed except that the PEG was present at a concentration of 10 wt %. Determination of the precipitate composition by analysis of the supernatant indicated a phycocyanin yield of 80 wt % with a 40 wt % purity in the precipitate.

While the neutral polymer (PEG) and the hemoglobin protein are substantially dissimilar in hydrophobic/hydrophilic character, the nonionic character difference between PEG (relatively hydrophobic) and the interaction product of DEAE-Dextran and phycocyanin (relatively hydrophilic as indicated by the dextran backbone) effected an enhancement in phycocyanin precipitation by increasing the yield. Indeed, there was no precipitation in the absence of PEG and increased precipitation at 10 wt % as compared to that observed at the 5 wt % PEG concentration of Example 11.

EXAMPLE 14

The procedure outlined in Example 12 was followed except that Dextran (ave. MW~70,000) was used in place of PEG at a concentration of 10 wt %. Determination of the precipitate composition by analysis of the supernatant indicated a phycocyanin yield of 34 wt % with a 80 wt % purity in the precipitate.

EXAMPLE 15

The procedure outlined in Example 14 was followed except that the dextran was present at a concentration of 20 wt %. Determination of the precipitate composition by analysis of the supernatant indicated a phycocyanin yield of 67 wt % with a purity of 75 wt % in the precipitate.

As contrasted with Examples 11 and 12, the neutral polymer dextran possessed similar hydrophylic/hydrophobic character to that of the hemoglobin protein (hydrophilic). Use of this neutral polymer resulted in higher selectivity than did PEG as indicated by higher purity of the resulting precipitate. In addition, the 20 wt % dextran resulted in a substantially higher yield than the 10 wt % trial (Example 13) while maintaining essentially the same purity.

COMPARATIVE EXAMPLES E & F

The procedure outlined in Example 12 was followed except that DEAE-Dextran and PEG were used separately. No precipitation occurred upon addition of the DEAE-Dextran alone. Likewise, no precipitation occurred upo addition of the PEG alone.

I claim:

1. A method of separating a first polypeptide fraction from a second polypeptide fraction of a mixed solution containing said fractions which comprises admixing at least one neutral polymer and at least one charged polymer with said solution, said charged polymer being soluble in said mixed solution and interacting with said first fraction to form an interaction product which precipitates from solution, said neutral polymer being soluble in said mixed solution and enhancing the effectiveness of said charged polymer in precipitating said first fraction.

2. A method of claim 1 in which the mixed solution comprising the polypeptides is an aqueous solution.

3. A method of claim 2 in which the charged polymer is admixed with the solution in the presence of the neutral polymer.

4. A method of claim 2 in which the effectiveness of the charged polymer is enhanced by lowering the concentration of the charged polymer required to cause precipitation.

5. A method of claim 2 in which the effectiveness of the charged polymer is enhanced by increasing the selectivity of the charged polymer for precipitating said first fraction.

6. A method of claim 2 in which the mixed solution comprises a cell extract.

7. A method of claim 2 in which the mixed solution is a fermentation broth.

8. A method of claim 2 in which a biologically active polypeptide is separated from contaminating polypeptides.

9. A method of claim 2 in which a mammalian hormone is separated from contaminating polypeptides.

10. A method of claim 2 in which an avian hormone is separated from contaminating polypeptides.

11. A method of claim 2 in which a somatotropin is separated from contaminating polypeptides.

12. A method of claim 2 in which the charged and neutral polymers are chosen such that the neutral polymer is substantially similar in hydrophobic/hydrophilic character to said second fraction or substantially dissimilar in hydrophobic/hydrophilic character to the interaction product of said charged polymer and first fraction.

13. A method of claim 2 in which said second fraction is more hydrophobic than said interaction product and the neutral polymer is more like said second fraction than said interaction product in hydrophobic/hydrophilic character.

14. A method of claim 2 in which said interaction product is more hydrophobic than said second fraction and the neutral polymer is more like said second fraction than said interaction product in hydrophobic hydrophilic character.

15. A method of claim 2 in which the polypeptide fractions consist essentially of proteins.

16. A method of separating a bovine somatotropin fraction from a contaminating polypeptide fraction of a mixed solution which comprises admixing at least one neutral polymer and at least one charged polymer with said solution, said charged polymer being soluble in said mixed solution and interacting with one of the fractions thereby precipitating said fraction, said neutral polymer being soluble in said mixed solution and enhancing the effectiveness of said charged polymer in precipitating said fraction.

17. A method of claim 16 in which the mixed solution comprising the bovine sometotropin fraction is an aqueous solution.

18. A method of claim 17 in which the contaiminating proteins are precipitated by the addition of diethylaminoethyldextran and the effectiveness of said diethylaminoethyldextran is enhanced by the addition of polyethylene glycol.

19. A method of claim 17 in which the contaminating proteins are precipitated by the addition of diethylaminoethyldextran and the effectiveness of said diethylaminoethyldextran is enhaneed by the addition of polypropylene glycol.

20. A method of claim 17 in which the contaminating proteins are precipitated by the addition of diethylaminoethyldextran and the effectiveness of said diethylaminoethyldextran is enhanced by the addition of polyvinylalcohol.

21. A method of claim 17 in which the contaminating proteins are precipitated by the addition of polyehtyleneimine and the effectiveness of said polyethyleneimine is enhanced by the addition of polyethylene glycol.

22. A method of claim 17 in which the contaminating proteins are precipitated by the addition of a cationic polyamine and the effectiveness of said cationic polyamine is enhanced by the addition of polyethylene glycol.

23. A method of claim 17 in which N-methionyl bovine somatotropin is separated by the precipitation of the contaminating proteins by the addition of diethylaminoethyldextran and the effectiveness of said diethylainoethyldextran is enhanced by the addition of polyethylene glycol.

24. A method of claim 17 in which N-methionyl bovine somatotropin is separated from contaminating *E. coli* proteins by the addition of diethylaminoethyldextran and the effectiveness of said diethylaminoethyldextran is enhanced by the additional of polyethylene glycol.

25. A method of claim 24 in which the separation is conducted at a solution pH between about 9 and 12.

* * * * *